United States Patent
Baudy

Patent Number: 5,525,600
Date of Patent: Jun. 11, 1996

[54] (THIOPHEN-2-YL)-PIPERIDIN OR TETRAHYDROPYRIDIN CARBOXAMIDES

[75] Inventor: Reinhardt B. Baudy, Yardley, Pa.

[73] Assignee: American Home Products Corporation, Madison, N.J.

[21] Appl. No.: 345,188

[22] Filed: Nov. 28, 1994

[51] Int. Cl.⁶ .......................... A61K 31/55; C07D 409/14
[52] U.S. Cl. ............................................. 514/212; 540/597
[58] Field of Search .............................. 540/597; 514/212

[56] References Cited

U.S. PATENT DOCUMENTS 4,988,814  1/1991  Abou-Gharbia et al. ............... 544/295

FOREIGN PATENT DOCUMENTS

| 2272436 | 5/1994 | United Kingdom . |
| 94/03444 | 2/1994 | WIPO . |
| WO94/08983 | 4/1994 | WIPO . |

*Primary Examiner*—Philip I. Datlow
*Attorney, Agent, or Firm*—Arnold S. Milowsky

[57] ABSTRACT

This invention provides compounds having the structure

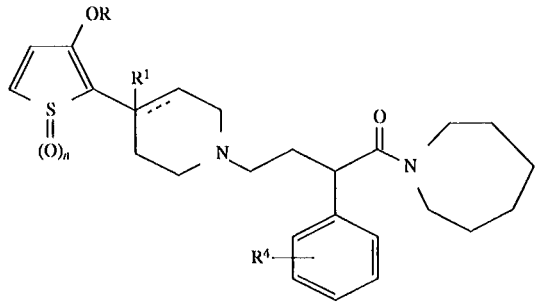

wherein
R is hydrogen, alkyl, alkenyl, alkynyl, —COR², phenyl, or phenylalkyl of 7–10 carbon atoms;
the dotted line represents an optional double bond;
R¹ is hydrogen, —OH, OR³, or is absent if the optional double bond is present;
R² and R³ are each, independently, alkyl, alkenyl, alkynyl, phenyl, or phenylalkyl;
R⁴ is hydrogen, —OR⁵, alkyl, alkenyl, alkynyl, —COR⁵, —CO₂R⁵, —CONR⁵R⁶, perhaloalkyl, halogen, phenyl, or phenylalkyl;
R⁵ and R⁶ are each, independently, hydrogen, alkyl, alkenyl, alkynyl, phenyl, or phenylalkyl; and
n=0–2
or a pharmaceutically acceptable salt thereof that are useful as antipsychotic, antidepressant and anxiolytic agents useful in the treatment and relief of the symptoms of these disease states.

14 Claims, No Drawings

(THIOPHEN-2-YL)-PIPERIDIN OR TETRAHYDROPYRIDIN CARBOXAMIDES

This invention provides compounds having selectivity for the serotonergic 5-HT$_{1A}$ receptor, useful in the treatment of central nervous system disorders, having the structure

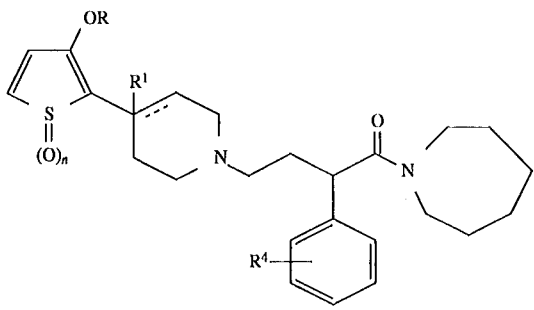

wherein
R is hydrogen, alkyl of 1–6 carbon atoms, alkenyl of 2–7 carbon atoms, alkynyl of 2–7 carbon atoms, —COR$^2$, phenyl, or phenylalkyl of 7–10 carbon atoms;
the dotted line represents an optional double bond;
R$^1$ is hydrogen, —OH, OR$^3$, or is absent if the optional double bond is present;
R$^2$ and R$^3$ are each, independently, alkyl of 1–6 carbon atoms, alkenyl of 2–7 carbon atoms, alkynyl of 2–7 carbon atoms, phenyl, or phenylalkyl of 7–10 carbon atoms;
R$^4$ is hydrogen, —OR$^5$, alkyl of 1–6 carbon atoms, alkenyl of 2–7 carbon atoms, alkynyl of 2–7 carbon atoms, —COR$^5$, —CO$_2$R$^5$, —CONR$^5$R$^6$, perhaloalkyl of 1–6 carbon atoms, halogen, phenyl, or phenylalkyl of 7–10 carbon atoms;
R$^5$ and R$^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and
n=0–2
or a pharmaceutically acceptable salt thereof.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The terms alkyl of 1–6 carbon atoms, alkenyl of 2–7 carbon atoms, and alkynyl of 2–7 carbon atoms, include both straight chain as well as branched carbon chains. In the generic structure described above, when n= 0, the sulfur containing ring is a thiophene ring, when n= 1, the sulfur containing ring is a thiophene S-oxide, and when n= 2, the sulfur containing ring is a thiophene S-dioxide. The term "halogen" refers to fluoro, chloro, bromo, or iodo.

The compounds within the scope of the invention by virtue of their configuration, exhibit stereoisomerism. Such centers can contain either the R or S configuration or can be racemic with respect to such center or centers. Accordingly, the compounds of the invention include the diastereomers, enantiomers, racemates and mixtures thereof.

Of these compounds, the preferred members are those in which n= 0; and those in which n= 0, and R is alkyl of 1–6 carbon atoms.

The compounds of this invention can be prepared by conventional methods. For example, the appropriately substituted 2-bromo-thiophene can be subjected to a Grignard reaction in which the addition to a 4-piperidone carbamate affords the desired tertiary alcohol. Subsequent hydrolysis of the carbamate yields the desired 4-hydroxy- 4-thiophen-2-yl-piperidine (1).

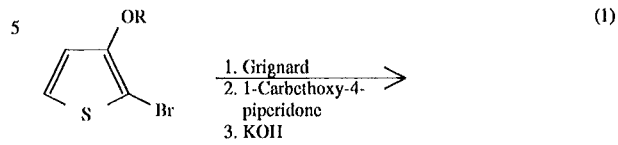

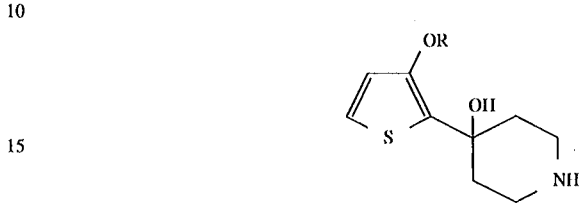

The 4-substituted piperidine can then be alkylated with a substituted 4-halobutanoic acid amide in the presence of an acid scavenger such as diisopropylethylamine to yield the final product (2).

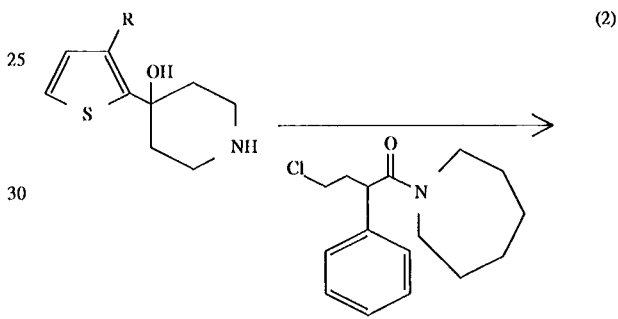

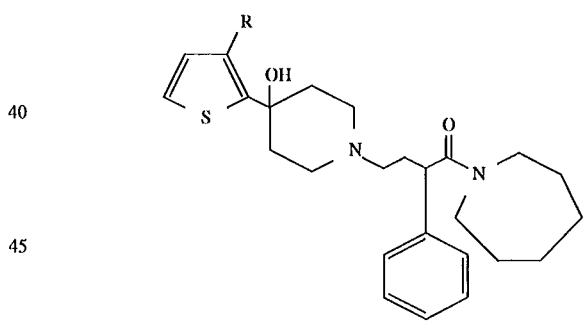

Further functionalization of the piperidine hydroxyl group can be accomplished using standard methodology, and dehydration of the hydroxyl group to provide tetrahydropyridine derivatives can be accomplished under mildly acidic conditions.

Representative compounds of this invention were evaluated and determined to have high affinity for the serotonin 5-HT$_{1A}$ receptor by evaluating the compound's ability to displace [$^3$H] 8-OHDPAT (dipropylaminotetralin) from the 5-HT$_{1A}$ serotonin receptor following the procedure of Hall et al., J. Neurochem. 44, 1685 (1985). This standard pharmacological test procedure was employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maelen et al., Eur. J. Pharmacol. 1986, 129 (1–2) 133–130). In this standard pharmacological test procedure, buspirone has an $IC_{50}$ of approximately 10 nM.

The results obtained for representative compounds of this invention in the standard pharmacological test procedure described above, are as follows:

| Compound | 5-$HT_{1A}$ Binding ($IC_{50}$) |
| --- | --- |
| Example 1 | 0.8 nM |
| Example 2 | 0.25 nM |
| Example 3 | 0.98 nM |
| Example 4 | 0.2 nM |
| Example 5 | 0.7 nM |

The results obtained in the standard pharmacological test procedure demonstrate that the compounds this invention possess high affinities for the serotonin 5-$HT_{1A}$ receptor, and consequently, they are useful in the treatment of multi-CNS disorders amenable to treatment with antipsychotic, antidepressant and anxiolytic agents. As such, the compounds of this invention may be administered a mammal in need of antipsychotic, antidepressant and/or anxiolytic medical treatment in an amount sufficient to alleviate the symptoms of the disease state, such as depression, paranoia, schizophrenia, anxiety, sleep disorders, eating disorders, cognitive disorders, panic, social phobia, obsessive compulsive disorders, sexual dysfunction, addiction, and related problems. When administered for the treatment of the above disease states, the compounds of this invention can be administered to a mammal orally, parenterally, intranasally, intrabronchially, transdermally, intravaginally, or rectally.

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage to be used in the treatment of a specific psychosis must be subjectively determined by the attending physician. The variables involved include the specific psychosis or state of anxiety or depression and the size, age and response pattern of the patient. Based on the results obtained in the standard pharmacological test procedures, projected oral daily dosages of active compound would be 1–100 mg/kg, preferably between 1–30 mg/kg, and more preferably between 1–10 mg/kg. Projected intravenous daily dosages would be 0.2–20 mg/kg, preferably between 0.2–6 mg/kg, and more preferably between 0.2–2 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantifies of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the production of representative compounds of this invention.

EXAMPLE 1

1-Azepan-1-yl-4-[4-hydroxy-4-(3-methoxy-thiophen-2-yl)-piperidin-1-yl]-2-phenyl-butan-1-one 0.75 hydroiodide.

A mixture of 4-hydroxy-4-(3-methoxy-thiophen-2-yl)-piperidine (2.4 g, 11 mmole), 1-(azepan-1-yl)-4-chloro-2- phenyl-butan-1-one (3.63 g, 13 mmole), diisopropyl-ethylamine (1.68 g, 13 mmole) and potassium iodide (2.16 g, 13 mmole) was heated in dimethylformamide (40 mL) to 80 ° C. for 4 hours. After cooling to ambient temperature the solvent was evaporated in vacuo and the residue suspended in ethyl acetate (80 mL). The precipitate was filtered and recrystallized from acetonitrile to yield 4.3 g of product, m.p. 126°–8 ° C.

Elemental Analysis for: $C_{26}H_{36}N_2O_3S.0.75$ HI.
Calcd: C, 56.51; H, 6.70; N, 5.07.
Found: C, 56.28; H, 6.43; N, 4.88.

EXAMPLE 2

1-Azepan-1-yl-4-[4-(3-methoxy-thiophen-2-yl)-1,2,3,6-tetrahydro-pyridin-1-yl]-2-phenyl-butan-1-one The title compound was prepared from 1-azepan-1-yl-4-[4-hydroxy-4-(3-methoxy-thiophen- 2-yl)-piperidin-1-yl]-2-phenyl-butan-1-one (1.35 g, 2.9 mmole) and acetic acid (80 mL) in the manner previously described above to yield 1.1 g of product, m.p. 108°–12 ° C.

Elemental Analysis for: $C_{26}H_{34}N_2O_2S.0.1$ chloroform.
Calcd: C, 69.49; H, 7.64; N, 6.23.
Found: C, 69.83; H, 7.47; N, 6.10.

EXAMPLE 3

1-Azepan-1-yl-4-[4-(3-methoxy-thiophen-2-yl)-piperidin-1-yl]-2-phenyl-butan- 1-one fumarate salt The title compound was prepared from 1-azepan-1-yl-4-[4-(3-methoxy-thiophen- 2-yl)-1,2,3,6-tetrahydro-pyridin-1-yl]-2-phenyl-butan-1-one (1 g, 2.2 mmole), acetic acid (50 mL), and Pearlman's catalyst (0.3 g) in the manner previously described above to yield 0.6 g of product, m.p. 134°–8 ° C. The title compound was isolated as a hemihydrate.

Elemental Analysis for: $C_{26}H_{36}N_2O_2S.C_8H_8H_8.0.5H_2O$.
Calcd: C, 59.90; H, 6.65; N, 4.11.
Found: C, 59.58; H, 6.71; N, 4.11.

EXAMPLE 4

(S)-1-Azepan-1-yl-4-[4-(3-methoxy-thiophen-2-yl)-1,2,3,6-tetrahydro-pyridin-1-yl]-2-phenyl-butan-1-one hydrochloride salt Acetic acid (0.48 mL) was added to a solution of the starting 4-hydroxy-4-(3-methoxy-thiophen- 2-yl)-piperidine (853 mg, 4 mmole) and (S)-4-(azepan-1-yl)-4-oxo- 3-phenyl-butyraldehyde (1037 rag, 4 mmole) in methanol (20 mL). At ambient temperature the reaction mixture was treated portionwise with sodium cyanoborohydride (276 mg, 4.4 mmole). The mixture was stirred an additional three hours at 25° C. and then poured into aqueous saturated sodium bicarbonate solution (50 mL). The aqueous phase was extracted with methylene chloride (3×50 mL). The combined organic extracts were washed with water (100 mL), brine (80 mL), dried over magnesium sulfate and filtered. The filtrate was evaporated in vacuo and the residue dissolved in chloroform (50 mL). Ethanolic hydrochloric acid was added and the resulting solution evaporated. The residue was triturated in ether and the precipitate filtered and dried to yield 400 mg of the title compound, mp 114°–6° C. The title compound was isolated as the hydrate.

Elemental Analysis for: $C_{26}H_{34}N_2O_2S.1HCl.1H_2O$.
Calcd: C, 63.30; H, 7.56; N, 5.68.
Found: C, 63.20 H, 7.68; N, 5.66.

EXAMPLE 5

(2S)-1-(Azepan-1-yl)-4-[4-(3-methoxy-thiophen-2-yl)-piperidin-1-yl]-2 -phenyl-butan- 1-one dihydrochloride salt A solution of (S)-1-Azepan-1-yl-4-[4-(3-methoxy-thiophen-2-yl)-1,2,3,6-tetrahydro-pyridin- 1-yl]-2-phenyl-butan-1-one (600 mg, 1.3 mmole) in glacial acetic acid (100 mL) was treated at once with Pearlman's Catalyst (600 mg) and hydrogenated at 50 psi at ambient temperature for 12 hours. After purging the reaction vessel with nitrogen the catalyst was removed by filtration, washed with acetic acid (30 mL) and the filtrate evaporated in vacuo. The residue was partitioned between 5% aqueous sodium bicarbonate (50 mL) and chloroform (100 mL). The separated organic layer was dried over magnesium sulfate, filtered and the filtrate evaporated to dryness in vacuo. Column chromatography on 20 g of silica gel with 3% methanol/chloroform as eluant, followed by trituration in ether with the addition of ethanolic hydrochloric acid gave 110 mg of the title compound, m.p. 91°–3 ° C.

Elemental Analysis for: $C_{26}H_{36}N_2O_2S.2HCl$
Calcd: C, 60.80; H, 7.45; N, 5.45.
Found: C, 61.19; H, 7.75; N, 5.43.

What is claimed is
1. A compound having the structure

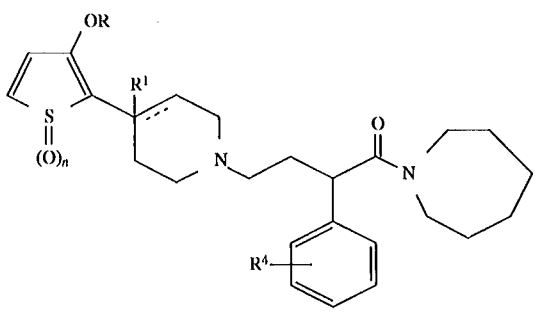

wherein
R is hydrogen, alkyl of 1–6 carbon atoms, alkenyl of 2–7 carbon atoms, alkynyl of 2–7 carbon atoms, —COR$^2$, phenyl, or phenylalkyl of 7–10 carbon atoms;
the dotted line represents an optional double bond;
R$^1$ is hydrogen, —OH, OR$^3$, or is absent if the optional double bond is present;
R$^2$ and R$^3$ are each, independently, alkyl of 1–6 carbon atoms, alkenyl of 2–7 carbon atoms, alkynyl of 2–7 carbon atoms, phenyl, or phenylalkyl of 7–10 carbon atoms;
R$^4$ is hydrogen, —OR$^5$, alkyl of 1–6 carbon atoms, alkenyl of 2–7 carbon atoms, alkynyl of 2–7 carbon atoms, —COR$^5$, —CO$_2$R$^5$, —CONR$^5$R$^6$, perhaloalkyl of 1– 6 carbon atoms, halogen, phenyl, or phenylalkyl of 7–10 carbon atoms;
R$^5$ and R$^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and
n=0–2
or a pharmaceutically acceptable salt thereof.

2. The compound of claim 1, wherein n= 0 or a pharmaceutically acceptable salt thereof.

3. The compound of claim 2, wherein R is alkyl of 1–6 carbon atoms or a pharmaceutically acceptable salt thereof.

4. The compound of claim 1 which is 1-azepan-1-yl-4-[4-hydroxy-4-(3-methoxy-thiophen- 2-yl)-piperidin-1-yl]-2-phenyl-butan-1-one or a pharmaceutically acceptable salt thereof.

5. The compound of claim 1 which is 1-azepan-1-yl-4-[4-hydroxy-4-(3-methoxy-thiophen- 2-yl)-piperidin-1-yl]-2-phenyl-butan-1-one hydroiodide salt.

6. The compound of claim 1 which is 1-azepan-1-yl-4-[4-(3-methoxy-thiophen-2-yl)- 1,2,3,6-tetrahydro-pyridin-1-yl]-2-phenyl-butan-1-one or a pharmaceutically acceptable salt thereof.

7. The compound of claim 1 which is 1-azepan-1-yl-4-[4-(3-methoxy-thiophen-2-yl)-piperidin- 1-yl]-2-phenyl-butan-1-one or a pharmaceutically acceptable salt thereof.

8. The compound of claim 1 which is 1-azepan-1-yl-4-[4-(3-methoxy-thiophen-2-yl)-piperidin- 1-yl]-2-phenyl-butan-1-one fumarate salt.

9. The compound of claim 1 which is (S)-1-azepan-1-yl-4-[4-(3-methoxy-thiophen- 2-yl)-1,2,3,6-tetrahydro-pyridin-1-yl]-2-phenyl-butan-1-one or a pharmaceutically acceptable salt thereof.

10. The compound of claim 1 which is (S)-1-azepan-1-yl-4-[4-(3-methoxy-thiophen- 2-yl)-1,2,3,6-tetrahydro-pyridin-1-yl]-2-phenyl-butan-1-one hydrochloride salt.

11. A compound of claim 1 which is (2S)-1-(azepan-1-yl)-4-[4-(3-methoxy-thiophen- 2-yl)-piperidin-1-yl]-2-phenyl-butan-1-one or a pharmaceutically acceptable salt thereof.

12. A compound of claim 1 which is (2S)-1-(azepan-1-yl)-4-[4-(3-methoxy-thiophen- 2-yl)-piperidin-1-yl]-2-phenyl-butan-1-one dihydrochloride salt.

13. A method of treating anxiety, psychosis, or depression in a mammal in need thereof which comprises administering to said mammal, an effective amount of a compound of the structure

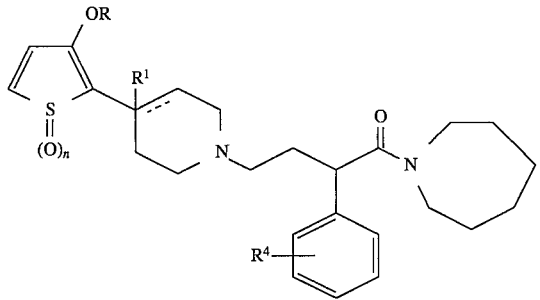

wherein

R is hydrogen, alkyl of 1–6 carbon atoms, alkenyl of 2–7 carbon atoms, alkynyl of 2–7 carbon atoms, —COR$^2$, phenyl, or phenylalkyl of 7–10 carbon atoms;

the dotted line represents an optional double bond;

R$^1$ is hydrogen, —OH, OR$^3$, or is absent if the optional double bond is present;

R$^2$ and R$^3$ are each, independently, alkyl of 1–6 carbon atoms, alkenyl of 2–7 carbon atoms, alkynyl of 2–7 carbon atoms, phenyl, or phenylalkyl of 7–10 carbon atoms;

R$^4$ is hydrogen, —OR$^5$, alkyl of 1–6 carbon atoms, alkenyl of 2–7 carbon atoms, alkynyl of 2–7 carbon atoms, —COR$^5$, —CO$_2$R$^5$, —CONR$^5$R$^6$, perhaloalkyl of 1–6 carbon atoms, halogen, phenyl, or phenylalkyl of 7–10 carbon atoms;

R$^5$ and R$^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and n=0–2 or a pharmaceutically acceptable salt thereof.

14. A pharmaceutical composition which comprises a compound of the structure

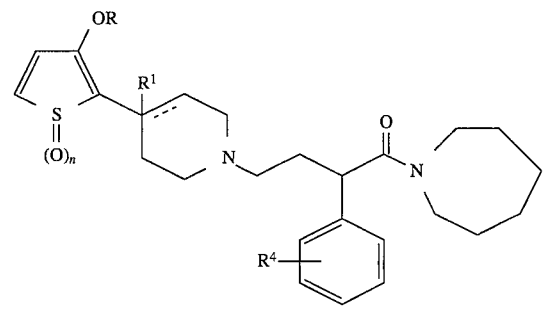

wherein

R is hydrogen, alkyl of 1–6 carbon atoms, alkenyl of 2–7 carbon atoms, alkynyl of 2–7 carbon atoms, —COR$^2$, phenyl, or phenylalkyl of 7–10 carbon atoms;

the dotted line represents an optional double bond;

R$^1$ is hydrogen, —OH, OR$^3$, or is absent if the optional double bond is present;

R$^2$ and R$^3$ are each, independently, alkyl of 1–6 carbon atoms, alkenyl of 2–7 carbon atoms, alkynyl of 2–7 carbon atoms, phenyl, or phenylalkyl of 7–10 carbon atoms;

R$^4$ is hydrogen, —OR$^5$, alkyl of 1–6 carbon atoms, alkenyl of 2–7 carbon atoms, alkynyl of 2–7 carbon atoms, —COR$^5$, —CO$_2$R$^5$, —CONR$^5$R$^6$, perhaloalkyl of 1– 6 carbon atoms, halogen, phenyl, or phenylalkyl of 7–10 carbon atoms;

R$^5$ and R$^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and n=0–2 or a pharmaceutically acceptable salt thereof, and a pharmaceutical carrier.

* * * * *